United States Patent
Mishima et al.

(10) Patent No.: US 6,824,534 B2
(45) Date of Patent: Nov. 30, 2004

(54) DISPOSABLE DIAPER (75) Inventors: Yoshitaka Mishima, Kagawa-ken (JP); Nariaki Shimoe, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/306,603

(22) Filed: May 6, 1999

(65) Prior Publication Data

US 2002/0013567 A1 Jan. 31, 2002

(30) Foreign Application Priority Data

May 8, 1998 (JP) ............................................ 10-126396

(51) Int. Cl.[7] .............................................. A61F 13/20
(52) U.S. Cl. ......................... 604/385.01; 604/385.101
(58) Field of Search ........................... 604/378, 385.12, 604/385.26, 385.16, 395, 358, 385.01, 385.101, 385.23

(56) References Cited

U.S. PATENT DOCUMENTS

| | | | | |
|---|---|---|---|---|
| 3,967,623 A | * | 7/1976 | Butterworth et al. | 128/287 |
| 5,431,643 A | * | 7/1995 | Ouellette et al. | 604/385.1 |
| 5,527,300 A | * | 6/1996 | Sauer | 604/378 |
| 5,624,421 A | * | 4/1997 | Dabi et al. | 604/378 |
| 5,990,377 A | * | 11/1999 | Chen et al. | 604/381 |

FOREIGN PATENT DOCUMENTS

| | | | | |
|---|---|---|---|---|
| GB | 2 284 831 | * | 5/1995 | A61F/13/15 |
| JP | 8-322878 | | 12/1996 | |

* cited by examiner

Primary Examiner—John J. Calvert
Assistant Examiner—Michele Kidwell
(74) Attorney, Agent, or Firm—Butzel Long (57) ABSTRACT

A disposable diaper is formed on its inner surface approximately in its longitudinally rear half area with a plurality of protuberances extending transversely across this rear half and intermittently arranged longitudinally of the diaper to thereby prevent loose fecal material from flowing forward and from leaking from a rear end of the diaper.

12 Claims, 5 Drawing Sheets

DISPOSABLE DIAPER

BACKGROUND OF THE INVENTION

The present invention relates to disposable diapers for absorption and containment of excretions.

Japanese Patent Application Disclosure Gazette No. Hei8-322878 disclose a disposable diaper partitioned in a crotch region of the diaper into front and rear halves. According to this disclosure, loose fecal material discharged on a zone of the crotch region extending in the vicinity of a front waist region of the diaper is prevented from flowing forward and thereby the wearer's urinal organs is prevented from being soiled with the loose fecal material.

However, it is impossible for the diaper to intercept an amount of loose fecal material tending to flow toward a rear waist region of the diaper. The amount of loose fecal material prevented from flowing forward correspondingly accelerates the loose fecal material to arrive at an end of the rear waist region and may often leak beyond the end of the rear waist region. This situation may occur particularly when the wearer is lying on his or her side.

SUMMARY OF THE INVENTION

In view of the problem as has been described above, it is an object of the present invention to provide a disposable diaper adapted to intercept the flow of loose fecal material, i.e., the flow of loose fecal material toward a rear waist region of the diaper.

According to the present invention, there is provided a disposable diaper having a front waist region, a rear waist region and a crotch region extending therebetween, the diaper comprising a liquid-pervious topsheet, a liquid-impervious backsheet and a liquid-absorbent core disposed therebetween, wherein: the diaper is formed on an inner surface thereof approximately in a longitudinally rear half area thereof with a plurality of protuberances extending transversely across the rear half area and intermittently arranged longitudinally of the diaper.

According to an embodiment of the present invention, each of the protuberances has a height locally decreased so as to form a groove extending longitudinally of the diaper.

According to another embodiment of the present invention, the protuberances comprise an absorbent material and a liquid-pervious sheet covering the absorbent material.

According to still another embodiment of the present invention, the liquid-pervious sheet is the topsheet.

According to further another preferred embodiment of the present invention, the protuberances comprise a sheet material configured so as to be risable up on the inner surface of the diaper.

DETAILED DESCRIPTION OF THE PREFERRED EMBODIMENTS

Details of a disposable diaper according to the present invention will be more fully understood from the description given hereunder with reference to the accompanying drawings.

Figure 1:
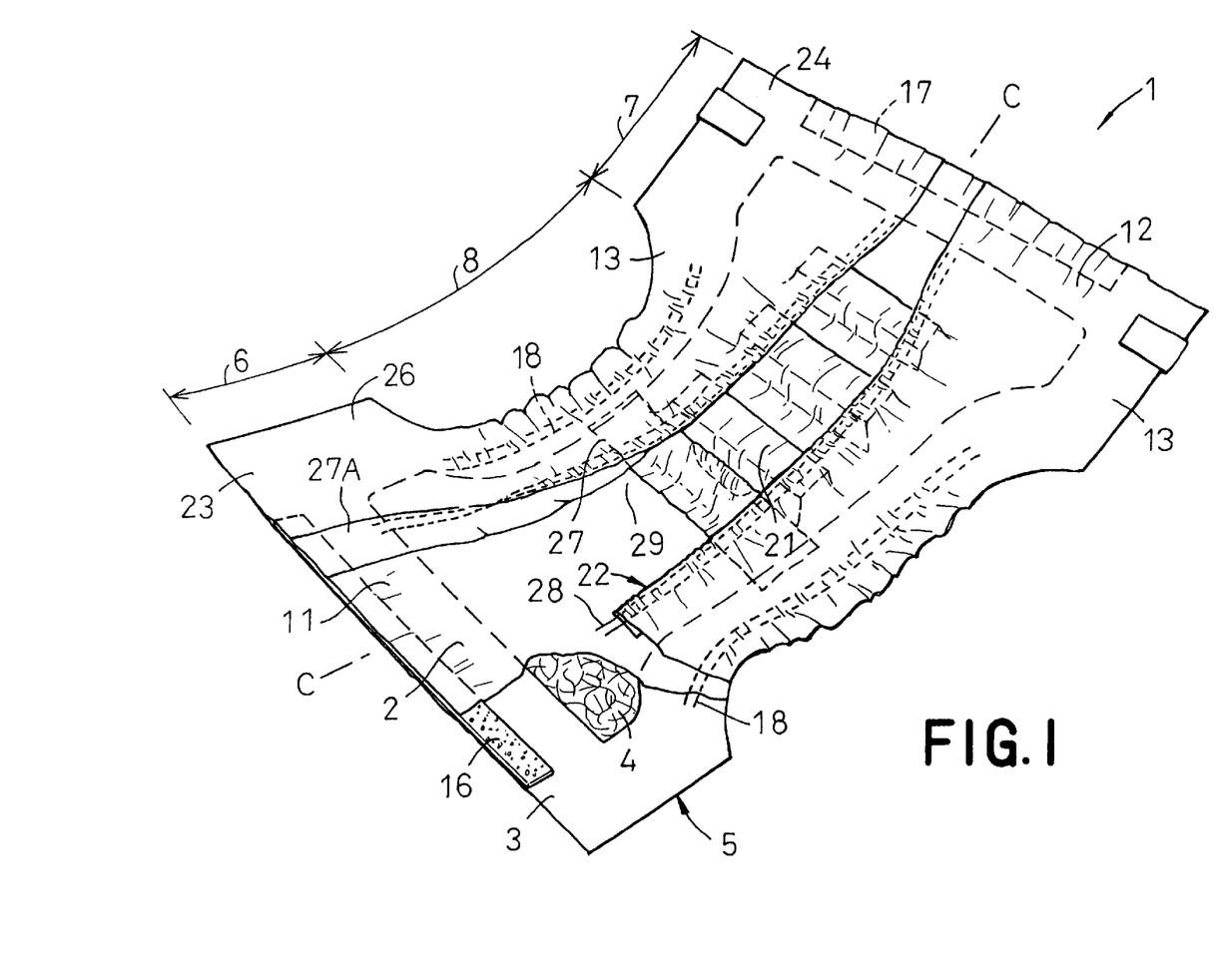
FIG. 1 is a perspective view of a disposable diaper constructed according to one embodiment of the present invention having a partly cut away portion.

Disposable diaper 1 shown by FIG. 1 in a perspective view having a partly cut away portion comprises a liquid-pervious topsheet 2, a liquid-impervious backsheet 3 and a liquid-absorbent core 4 disposed between these two sheets 2, 3, forming together a diaper basic structure 5. The basic structure 5 is longitudinally composed of a front waist region 6, a rear waist region 7 and a crotch region 8 extending between these two waist regions 6, 7. The topsheet 2 and the backsheet 3 extend outward beyond a peripheral edge of the core 4 and are placed upon and bonded to each other along their extensions so as to form longitudinally opposite ends 11, 12 and transversely opposite side edges 13, 13. Along the ends 11, 12, there are provided with elastic members 16, 17 extending circumferentially of the front and rear waist regions 6, 7, respectively, and along the side edges 13, 13, there are provided with elastic members 18, 18 extending around respective legs of a wearer. These elastic members 16, 17, 18, 18 are disposed between the topsheet 2 and the backsheet 3 and secured under appropriate tension to an inner surface of at least one of these two sheets 2, 3.

The basic structure 5 is formed on its inner surface approximately in its longitudinally rear half area with a plurality of protuberances 21 which extend transversely across the rear half area and are intermittently arranged longitudinally of the basic structure 5. The inner surface of the basic structure 5 is additionally formed along its transversely opposite side edges with a pair of barrier cuffs 22, respectively, extending longitudinally of the basic structure 5. Each of the barrier cuffs 22 has its front and rear ends 23, 24 joined to the longitudinally opposite ends 11, 12 of the diaper 1 and a proximal edge zone 26 joined to the corresponding side edge 13 of the diaper 1. The barrier cuffs 22 have distal edge zones 27 lying to a center line C—C transversely dividing the diaper 1 in two and partially covering the inner surface as well as the protuberances 21 of the basic structure 5. It should be understood here that a portion 27A of the distal edge zones 27 lying adjacent the front end 23 is folded back away from the center line C—C onto the corresponding portion of the proximal edge zone 26 and joined thereto. The distal edge zones 27 are provided with elastic members 28 longitudinally extending and secured thereto under appropriate tension. When the diaper 1 is longitudinally curved with its inner surface inside, the elastic members 28 contract and consequently the distal edge zones 27 rise up on their inner surfaces. As a result, a channel 29 formed between the distal edge zones 27 and the inner surface of the basic structure 5 is opened inwardly of the diaper 1.

Figure 2:
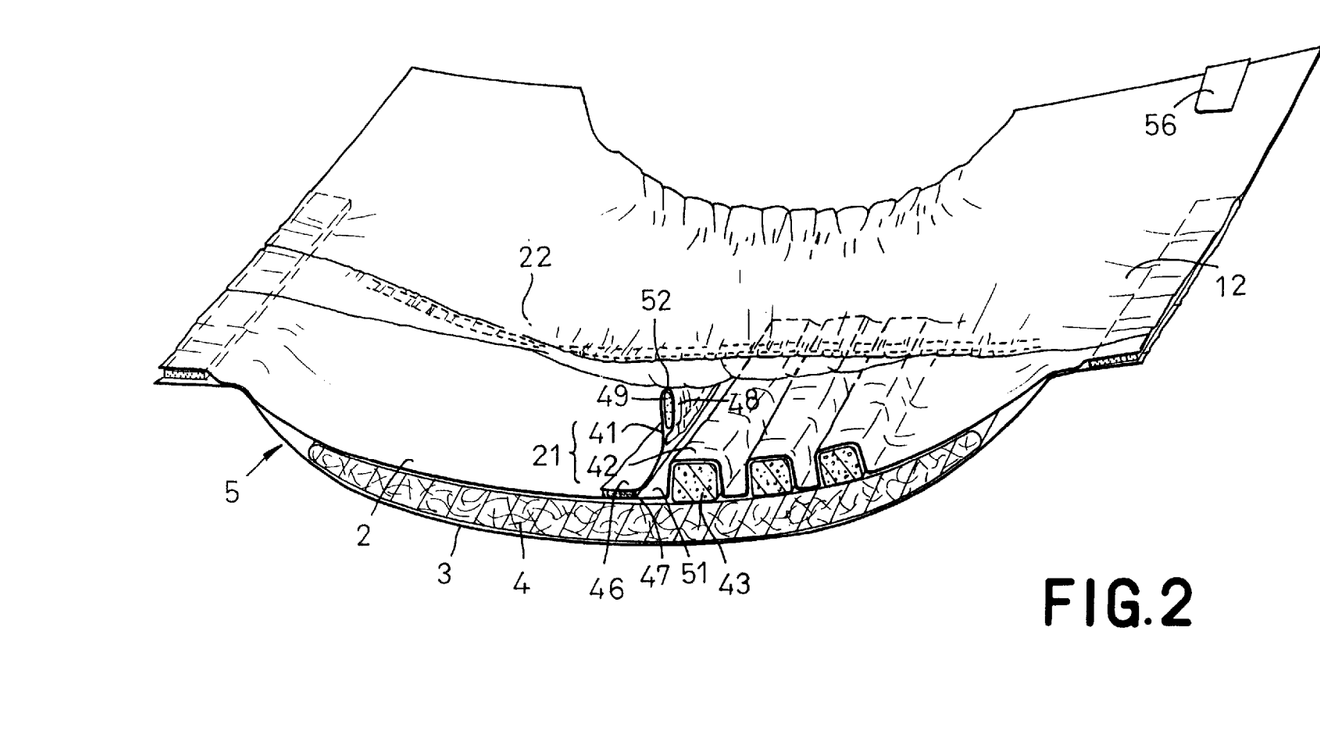
FIG. 2 is a perspective view of a section taken along a line C—C in FIG. 1.

FIG. 2 is a perspective view of the diaper 1 taken along the line C—C in FIG. 1. The protuberances 21 comprise a first protuberance 41 formed by a liquid-pervious or liquid-impervious sheet and a plurality of second protuberances 42 formed by absorbent cores 43 covered with the topsheet 2 so that the topsheet 2 undulates above the core 4. The first protuberance 41 is risable up on the inner surface of the basic structure 5 and extends across the basic structure substantially in its middle. The first and second protuberances 41, 42 are successively spaced one from another longitudinally of the diaper 1.

The first protuberance 41 has its lower edge 47 joined to the topsheet 2 by means of hot melt adhesive 47 and its upper edge 48 provided with an elastic member 49 extending transversely of the diaper 1. The elastic member 49 is covered with the sheet forming the first protuberance 41 and secured to the sheet under appropriate tension. Between the first protuberance 41 and the inner surface of the basic structure 5, a channel 51 is formed, which is adapted to be opened rearwardly of the diaper 1. When the diaper 1 is transversely curved with its inner surface inside, the elastic member 49 contracts whereupon the first protuberance 41 rises up on the inner surface of the basic structure 5 and the channel 51 is opened as shown. A crest 52 of the first protuberance 41 may be joined to the inner surface of the barrier cuff 22 which covers the crest 52, if desired. In this case, the first protuberance 41 necessarily rises up as the barrier cuff 22 rises.

The second protuberances 42 are formed by covering the corresponding number of cores 43 obtained by directly molding the core 4 of the basic structure 5 or by molding a suitable absorbent material separately of the core 4 with the topsheet 2. FIGS. 1 and 2 show an embodiment in which the absorbent material is molded separately of the core 4 to obtain the cores 43. It is also possible to form the second protuberances 42 by covering the cores 43 molded separately of the core 4 with a liquid-pervious sheet provided separately of the topsheet 2 and then by joining this assembly to the inner surface of the diaper 1.

The diaper 1 constructed as has been described above may be put on the wearer's body with a pair of tape fasteners 56 attached to the side edges 13, 13 of the rear waist region 7 being anchored onto the front waist region 6. With such diaper 1, even if loose fecal material is discharged thereon, it is effectively prevented from flowing forward and thereby the wearer's urinary organs is protected from being soiled with the loose fecal material because the diaper 1 is partitioned by the first protuberance 41 into front and rear halves. An amount of loose fecal material tending to flow rearward, i.e., toward the back of the wearer is reliably intercepted by a plurality of second protuberances 42 and prevented from leaking beyond the rear end 12 of the diaper 1. With the protuberances 21 containing therein a suitable absorbent material as the second protuberances 42 are so in the case of this embodiment, not only interception of the loose fecal material tending to flow rearwardly of the diaper 1 but also absorption of water contained in the loose fecal material is achieved. In this manner, the effect of preventing the loose fecal material from leaking beyond the rear end 12 is further ensured.

Figure 3:
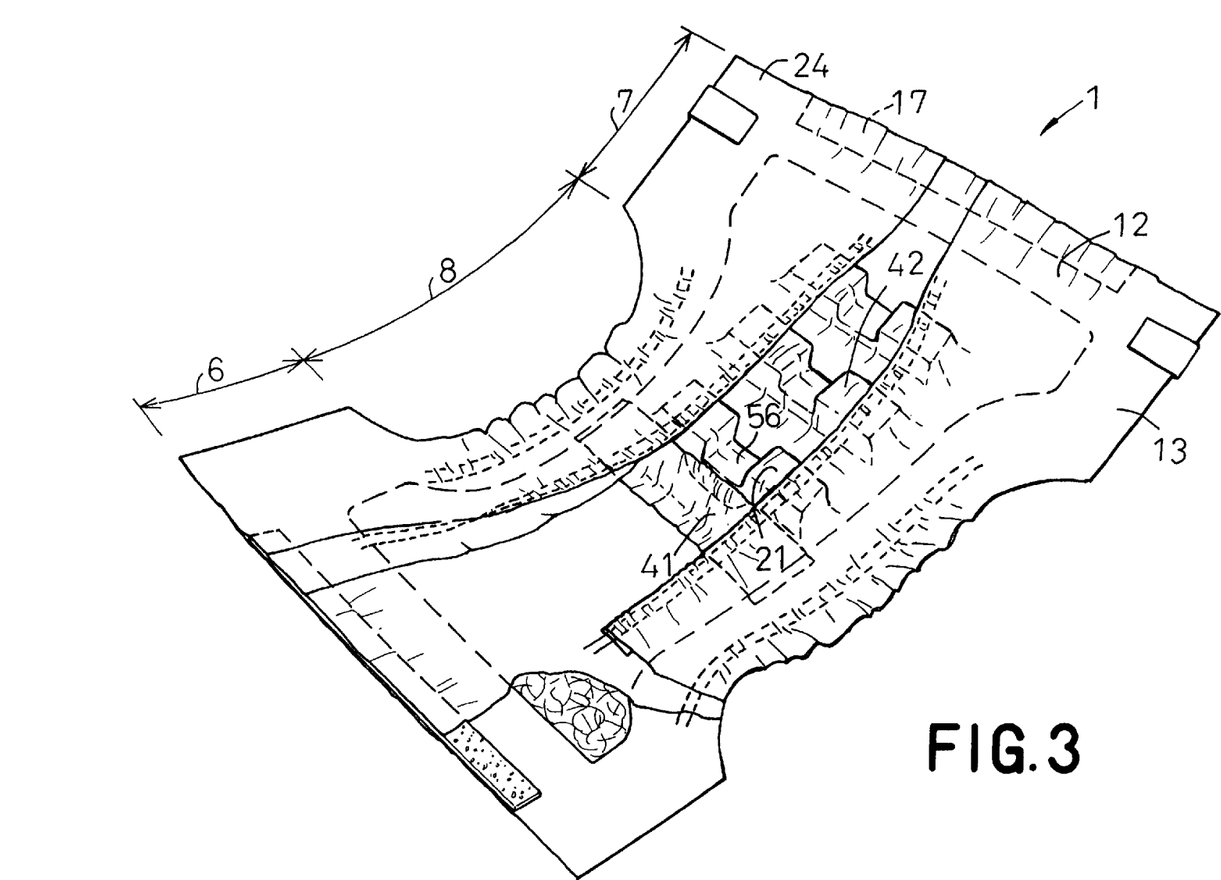
FIG. 3 is a view similar to FIG. 1 of another embodiment of the present invention.

FIG. 3 is a view similar to FIG. 1 showing another embodiment of the present invention. According to this embodiment of the diaper 1, the second protuberances 42 making a part of the protuberances 21 are formed with grooves 56 extending longitudinally of the diaper 1 by dimensioning a height of the respective protuberances 42 to be locally decreased. By permitting certain amount of the loose fecal material to flow rearwardly of the diaper 1 through the grooves 56, an effective area of the core 4 is enlarged over which an amount of water contained in the loose fecal material can be absorbed by the core 4. It is also possible to provide each of the second protuberances 42 with a plurality of the grooves 56.

Figure 4:
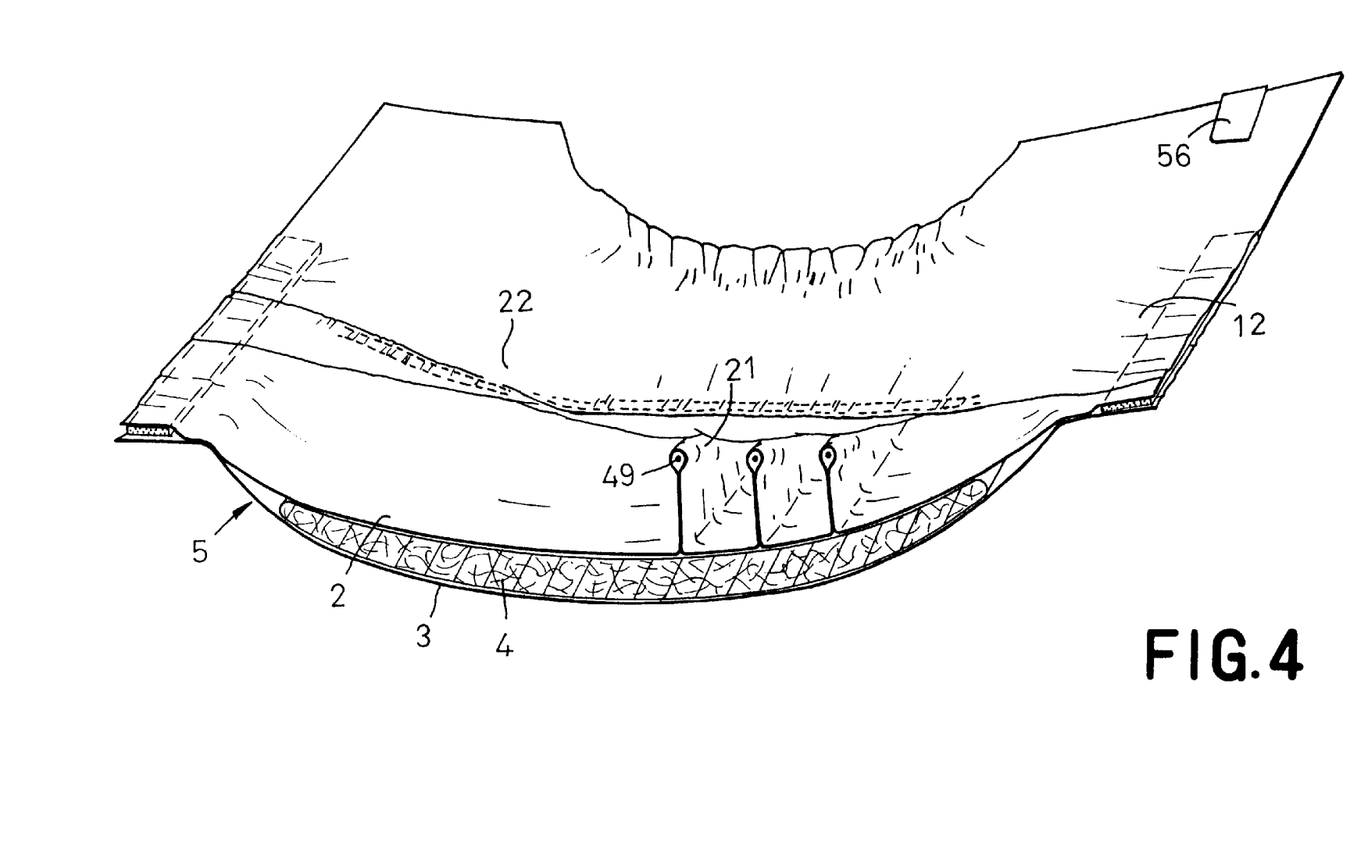
FIG. 4 is a view similar to FIG. 2 of still another embodiment of the present invention.
Figure 5:
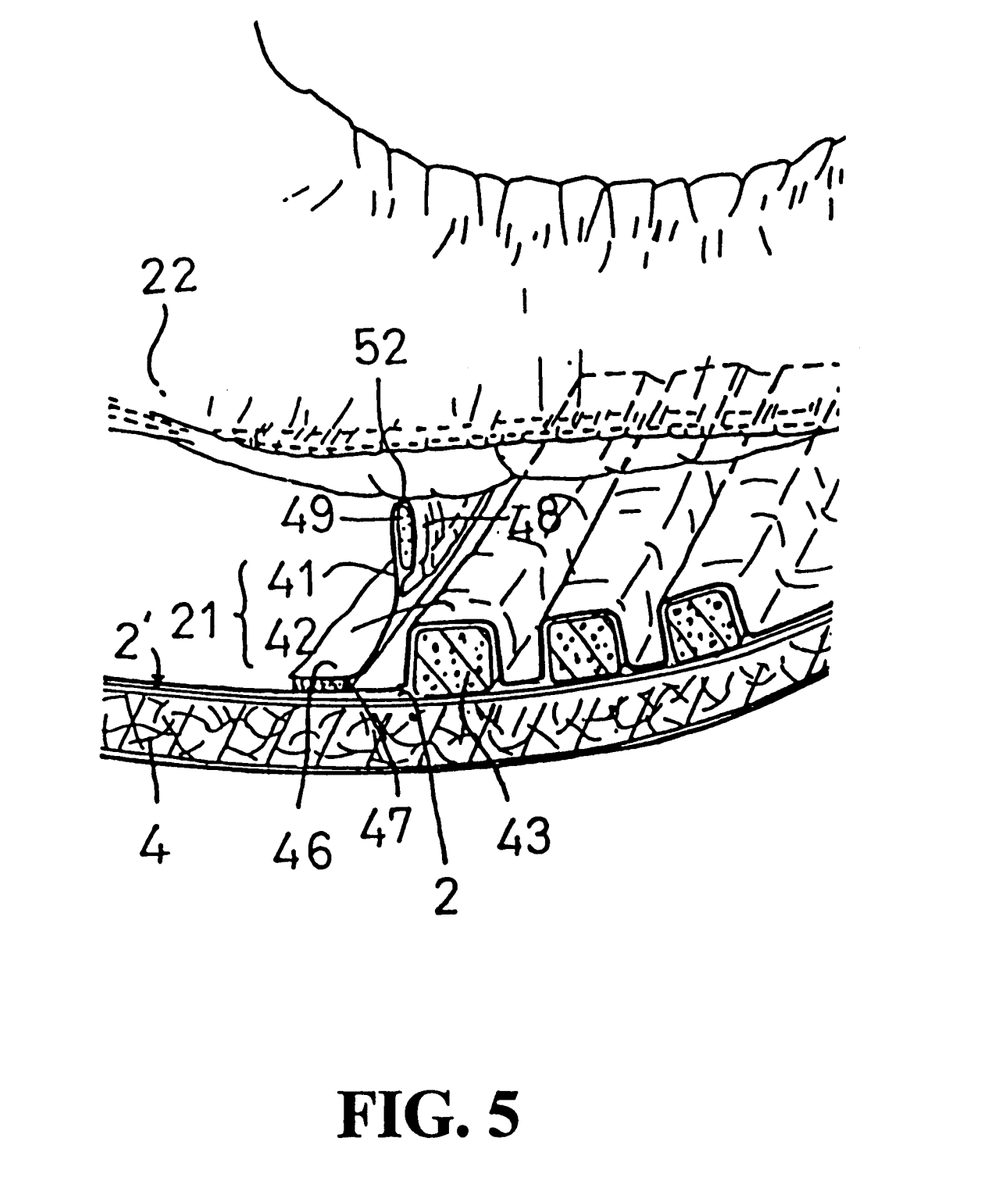
FIG. 5 is cross sectional view similar to FIG. 2 that depicts another embodiment of the invention.

FIG. 4 is a view similar to FIG. 2 showing still another embodiment of the present invention. According to this specific embodiment of the diaper 1, the topsheet 2 is utilized to form a plurality of pleats extending transversely of the diaper 1 so that these pleats form the protuberances 21. Specifically, the topsheet 2 is successively folded on itself and bonded together to form the protuberances 21. Each of the protuberances 21 contains within its crest an elastic member 49 extending transversely of the diaper 1 and secured under appropriate tension to an inner surface of the crest.

According to the present invention, suitable adhesive agents such as hot melt adhesive or suitable glue may be used to bond the respective members together. For the heat-sealable members, a heat-sealing technique may be used.

A prominent feature of a disposable diaper according to the present invention lies in that the diaper is formed on its inner surface approximately in its rear half area with a plurality of protuberances which extend transversely across the rear half area and are longitudinally spaced one from another. Such a unique arrangement ensures that the loose fecal material discharged thereon can be prevented not only from flowing forward but also from leaking beyond the rear end of the diaper. The protuberances containing therein a suitable absorbent material can further improve the effect of preventing the loose fecal material from leaking beyond the rear end of the diaper.

What is claimed is:

1. A disposable diaper comprising:
    a front waist region;
    a rear waist region;
    a crotch region extending between the front waist region and the rear waist region;
    a liquid-pervious topsheet that remains at least partially exposed to a wearer of the diaper;
    a liquid-impervious backsheet;
    a liquid-absorbent core disposed between the liquid-pervious topsheet and the liquid-impervious backsheet; and
    a plurality of protuberances formed on and rising up above a planar surface portion of the liquid-pervious topsheet approximately in a longitudinal rear half of the liquid-pervious topsheet, each of said plurality of protuberances comprising elongated structures that have a major dimension that extends in a transverse direction of the diaper, individual ones of said plurality of protuberances extending transversely across said rear half area and being intermittently ranged longitudinally of said diaper so that said plurality of protuberances are oriented and positioned to inhibit loose fecal material from flowing longitudinally, rear most ones of said plurality of protuberances having opposite transverse ends with are spaced inward from transverse side edges of said liquid-absorbent core, said plurality of protuberances further being fixed in position relative to the liquid-pervious topsheet.

2. The diaper according to claim 1, wherein said plurality of protuberances has a height that is locally decreased to form a groove which extends longitudinally of the diaper.

3. The diaper according to claim 1, wherein said plurality of protuberances comprise an absorbent material which is covered by a liquid-pervious sheet.

4. The diaper according to claim 1, wherein said plurality of protuberances comprise a sheet material configured to rise up on said topsheet of said diaper.

5. The diaper according to claim 1, wherein the plurality of protuberances comprises cores that are filled with an absorbent material.

6. The diaper according to claim 1 further comprising a pair of barrier cuffs extending longitudinally of said diaper, each of said pair of barrier cuffs having front and rear ends that are joined to longitudinally opposite ends of said diaper, a proximal edge zone joined to a corresponding side edge of said diaper and an elasticized distal edge zone lying along a center line that transversely divides said diaper in two, said pair of barrier cuffs partially covering said topsheet and said plurality of protuberances, wherein a portion of said distal edge zone of each of said barrier cuffs lying adjacent a front end of said diaper is folded back away from said center line onto a corresponding portion of said proximal edge zone and is joined thereto.

7. The diaper according to claim 1, wherein said plurality of protuberances comprises a first protuberance and a plurality of second protuberances, said first protuberance comprising a sheet material that rises up on said topsheet so as to extend upward beyond tops of said plurality of second protuberances and, said first protuberance being positioned in a longitudinal middle of said diaper, said plurality of second protuberances comprising an absorbent material that is covered by said topsheet and being positioned between said first protuberance and a rear end of said absorbent core in the rear waist region.

8. The diaper according to claim 2 further comprising a pair of barrier cuffs extending longitudinally of said diaper, each of said pair of barrier cuffs having front and rear ends that are joined to longitudinally opposite ends of said diaper, a proximal edge zone joined to a corresponding side edge of said diaper and an elasticized distal edge zone lying along a center line that transversely divides said diaper in two, said pair of barrier cuffs partially covering said topsheet, said first protuberance and said plurality of second protuberances, wherein a portion of said distal edge zone of each of said barrier cuffs lying adjacent a front end of said diaper is folded back away from said center line onto a corresponding portion of said proximal edge zone and is joined thereto.

9. A disposable diaper comprising:
   a front waist region;
   a rear waist region;
   a crotch region extending between the front waist region and the rear waist region;
   a liquid-pervious topsheet that remains at least partially exposed to a wearer of the diaper;
   a liquid-impervious backsheet;
   a liquid-absorbent core disposed between the liquid-pervious topsheet and the liquid-impervious backsheet; and
   a plurality of protuberances formed beneath the liquid-pervious topsheet approximately in a longitudinal rear half of the liquid-pervious topsheet, each of said plurality of protuberances comprising elongated structures that have a major dimension that extends in a transverse direction of the diaper, individual ones of said plurality of protuberances extending transversely across said rear half area and being intermittently arranged longitudinally of said diaper so that said plurality of protuberances are oriented and positioned to inhibit loose fecal material from flowing longitudinally, rear most ones of said plurality of protuberances having opposite transverse ends with are spaced inward from transverse side edges of said liquid-absorbent core, said plurality of protuberances further being fixed in position relative to the liquid-pervious topsheet,
   wherein said plurality of protuberances comprise an absorbent material that is covered by said liquid-pervious topsheet.

10. The diaper according to claim 4 further comprising a pair of barrier cuffs extending longitudinally of said diaper, each of said pair of barrier cuffs having front and rear ends that are joined to longitudinally opposite ends of said diaper, a proximal edge zone joined to a corresponding side edge of said diaper and an elasticized distal edge zone lying along a center line that transversely divides said diaper in two, said pair of barrier cuffs partially covering said topsheet and said plurality of protuberances, wherein a portion of said distal edge zone of each of said barrier cuffs lying adjacent a front end of said diaper is folded back away from said center line onto a corresponding portion of said proximal edge zone and is joined thereto.

11. The diaper according to claim 4, wherein said plurality of protuberances comprises a first protuberance and a plurality of second protuberances, said first protuberance comprising a sheet material that rises up on said topsheet so as to extend upward beyond tops of said plurality of second protuberances and, said first protuberance being positioned in a longitudinal middle of said diaper, said plurality of second protuberances comprising an absorbent material that is covered by said topsheet and being positioned between said first protuberance and a rear end of said absorbent core in the rear waist region.

12. The diaper according to claim 11 further comprising a pair of barrier cuffs extending longitudinally of said diaper, each of said pair of barrier cuffs having front and rear ends that are joined to longitudinally opposite ends of said diaper, a proximal edge zone joined to a corresponding side edge of said diaper and an elasticized distal edge zone lying along a center line that transversely divides said diaper in two, said pair of barrier cuffs partially covering said topsheet, said first protuberance and said plurality of second protuberance, wherein a portion of said distal edge zone of each of said barrier cuffs lying adjacent a front end of said diaper is folded back away from said center line onto a corresponding portion of said proximal edge zone and is joined thereto.

* * * * *

UNITED STATES PATENT AND TRADEMARK OFFICE
CERTIFICATE OF CORRECTION

PATENT NO. : 6,824,534 B2
DATED : November 30, 2004
INVENTOR(S) : Yoshitaka Mishima and Nariaki Shimoe It is certified that error appears in the above-identified patent and that said Letters Patent is hereby corrected as shown below:

<u>Column 4,</u>
Line 45, should be changed from "half area and being intermittently ranged longitudinally" to -- halt area and being intermittently arranged longitudinally --

Signed and Sealed this

Thirty-first Day of May, 2005

JON W. DUDAS
*Director of the United States Patent and Trademark Office*

UNITED STATES PATENT AND TRADEMARK OFFICE
CERTIFICATE OF CORRECTION

PATENT NO. : 6,824,534 B2
DATED : November 30, 2004
INVENTOR(S) : Yoshitaka Mishima and Nariaki Shimoe It is certified that error appears in the above-identified patent and that said Letters Patent is hereby corrected as shown below:

<u>Column 4,</u>
Line 45, should be changed from "half area and being intermittently ranged longitudinally" to -- half area and being intermittently arranged longitudinally --.

This certificate supersedes Certificate of Correction issued May 31, 2005.

Signed and Sealed this

Sixth Day of September, 2005

JON W. DUDAS
*Director of the United States Patent and Trademark Office*